United States Patent
Ryu et al.

(10) Patent No.: US 11,840,804 B2
(45) Date of Patent: Dec. 12, 2023

(54) PYRIDINE AND PYRIMIDINE SUBSTITUTED TRIAZINE UV ABSORBERS

(71) Applicant: Huntsman Advanced Materials (Switzerland) GMBH, Basel (CH)

(72) Inventors: Hosuk Ryu, Arlesheim (CH); Hans-Jorg Peter, Basel (CH); Gilles Sperissen, Eschentzwiller (FR); Martin Weber, Steinen (DE)

(73) Assignee: Huntsman Textile Effects (Switzerland) GmbH, Basel (CH)

( * ) Notice: Subject to any disclaimer, the term of this patent is extended or adjusted under 35 U.S.C. 154(b) by 402 days.

(21) Appl. No.: 17/280,944

(22) PCT Filed: Sep. 17, 2019

(86) PCT No.: PCT/EP2019/074848
§ 371 (c)(1),
(2) Date: Mar. 29, 2021

(87) PCT Pub. No.: WO2020/069851
PCT Pub. Date: Apr. 9, 2020

(65) Prior Publication Data
US 2021/0340705 A1    Nov. 4, 2021

(30) Foreign Application Priority Data

Oct. 3, 2018 (EP) ..................... 18198408

(51) Int. Cl.
*D06M 13/00* (2006.01)
*D06P 5/06* (2006.01)
(Continued)

(52) U.S. Cl.
CPC .............. *D06P 5/06* (2013.01); *C07D 401/04* (2013.01); *C07D 403/04* (2013.01); *C09K 15/30* (2013.01);
(Continued)

(58) Field of Classification Search
CPC .......... D06P 5/06; D06P 1/445; D06P 1/6426; D06P 3/52; D06P 3/42; D06P 3/54;
(Continued)

(56) References Cited

U.S. PATENT DOCUMENTS 6,004,965 A    12/1999    Breu et al.

FOREIGN PATENT DOCUMENTS

CN    101523239 B  * 10/2016    ............. G02C 7/108
EP    0468921 B2    7/1998
(Continued)

OTHER PUBLICATIONS

Brunetti H et al: "Die Synthese Von Asymmetrisch Substituierten O-Hydroxyphenyl-S-Triazinen", Helvetica Chimica Acta, Verlag Helvetica Chimica Acta, vol. 55, No. 5, Jan. 1, 1972 (Jan. 1, 1972), pp. 1566-1594, XP000651570, ISSN: 0018-019X, DOI: 10.1002/HLCA.19720550520 p. 1569 reaction of 6 and 11 to yield 10 B; p. 1571, reaction of 10B and 3.1 to yield 14B.
(Continued)

*Primary Examiner* — Eisa B Elhilo
(74) *Attorney, Agent, or Firm* — Christensen, Fonder, Dardi & Herbert

(57) ABSTRACT

A compound of formula

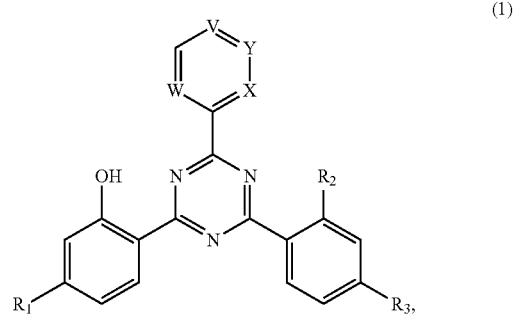

(1)

wherein V, W, X and Y represent N or CH, at least one of V, W, X and Y being N and at least two of V, W, X and Y being CH; and $R_1$, $R_2$ and $R_3$ are each independently of the other hydrogen, $C_1$-$C_8$alkyl, $C_1$-$C_8$alkoxy, nitro, cyano, trifluoromethyl, halogen or hydroxy;

with the proviso that the compounds of formulae

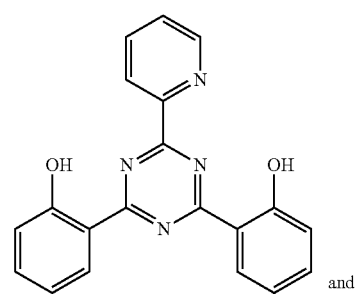

(101)

and
(Continued)

-continued

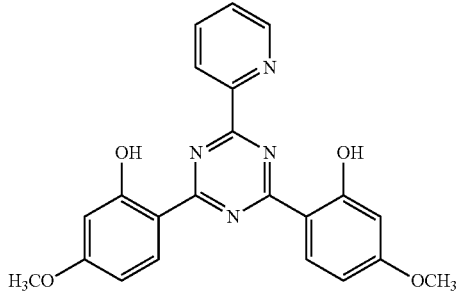
(102)

are excluded,
provides good lightfastness properties to textile fibre materials, in particular PES fibre materials.

8 Claims, No Drawings

(51) Int. Cl.
| | | |
|---|---|---|
| C07D 401/04 | (2006.01) | |
| C07D 403/04 | (2006.01) | |
| C09K 15/30 | (2006.01) | |
| D06M 13/358 | (2006.01) | |
| D06P 1/44 | (2006.01) | |
| D06P 1/642 | (2006.01) | |
| D06P 3/52 | (2006.01) | |
| D06M 101/32 | (2006.01) | |

(52) U.S. Cl.
CPC .......... *D06M 13/358* (2013.01); *D06P 1/445* (2013.01); *D06P 1/6426* (2013.01); *D06P 3/52* (2013.01); *D06M 2101/32* (2013.01); *D06M 2200/25* (2013.01)

(58) Field of Classification Search
CPC .... C07D 401/04; C07D 403/04; C09K 15/30; D06M 13/358; D06M 2101/32; D06M 2200/25; C09B 68/46775
USPC ........................................................... 8/688
See application file for complete search history.

(56) References Cited

FOREIGN PATENT DOCUMENTS

| EP | 0964096 A2 | 12/1999 | |
|---|---|---|---|
| EP | 1321812 A2 * | 6/2003 | ........... G03C 7/3005 |
| WO | WO 2005001568 A1 * | 1/2005 | ......... G03C 7/39276 |
| WO | 2011024056 A2 | 3/2011 | |

OTHER PUBLICATIONS

F. Waiblinger et.al.: "Ultraviolorbers and singlet oxygen", Journal of Photochemistry and Photobiology A: Chemistry, vol. 126, 1999, pp. 43-49, XP002789659, p. 43-44, pargaraph 1 introduction; p. 44, compound M-OH-P.

* cited by examiner

PYRIDINE AND PYRIMIDINE SUBSTITUTED TRIAZINE UV ABSORBERS

CROSS-REFERENCE TO RELATED APPLICATIONS

This application is the National Phase of International Application PCT/EP2019/074848 filed Sep. 17, 2019 which designated the U.S. and which claims priority to European App. Serial No. 18198408.9 filed Oct. 3, 2018. The noted applications are incorporated herein by reference.

The present invention relates to UV absorbing agents (UVA) derived from hydroxyphenyl-s-triazines, a process for their preparation and their use for the photochemical stabilisation of dyed or undyed textile materials.

The disperse dyes applied in the dyeing or printing of textile fibre materials, especially synthetic textile fibre materials, are in some cases substantially damaged when subject to the action of light, especially when simultaneously subject to the action of heat. In order to avoid such damage, UV absorbers (UVAs) are added to the dyeing liquors and printing pastes when dyeing fibres used in the automotive or swimwear sectors or in so-called "outdoor" articles.

EP-A 0 468 921 describes aqueous dispersions comprising a hydroxyphenyl-s-triazine as UVA, which are suitable as light stabilisers for textile fibres and which are distinguished by good transport and storage stability.

However, the ambitious requirements especially made by the automotive industry are not met to the full extent by the known triazine UVAs.

It has now been found that the application of triazine-based UVAs containing heteroaromatic substituents provides for excellent light fastness and hot light fastness properties.

The present invention relates to a compound of formula

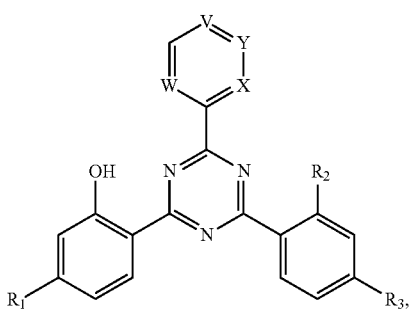

(1)

wherein V, W, X and Y represent N or CH, at least one of V, W, X and Y being N and at least two of V, W, X and Y being CH; and $R_1$, $R_2$ and $R_3$ are each independently of the other hydrogen, $C_1$-$C_8$alkyl, $C_1$-$C_8$alkoxy, nitro, cyano, trifluoromethyl, halogen or hydroxy;

with the proviso that the compounds of formulae

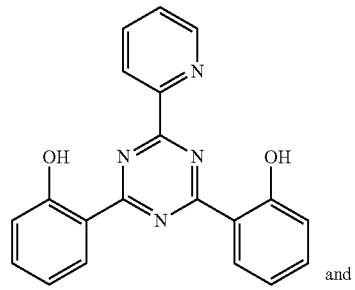

(101)

and

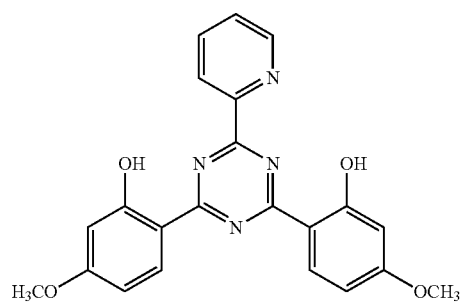

(102)

are excluded.

Alkyl and alkoxy groups as the radical $R_1$, $R_2$ or $R_3$ may be linear or branched.

Examples of alkyl groups are methyl, ethyl, n-propyl, isopropyl, n-butyl, sec-butyl, tert-butyl, isobutyl, n-pentyl, neopentyl, n-hexyl, 2-ethylhexyl, n-octyl and isooctyl.

Suitable alkoxy groups are, for example, methoxy, ethoxy, n-propoxy, isopropoxy, n-butoxy, sec-butoxy, tert-butoxy, isobutoxy, n-pentyloxy, neopentyloxy, n-hexyloxy, 2-ethylhexyloxy, n-octyloxy and isooctyloxy.

Halogen is, for example, fluorine, bromine or, preferably, chlorine.

Preference is given to a compound of formula (1) as defined above wherein X is N and V, W and Y are CH.

Further preference is given to a compound of formula (1) as defined above wherein Y is N and V, W and X are CH.

Further preferred compounds of formula (1) as defined above are those wherein V is N and W, X and Y are CH.

Further preference is given to a compound of formula (1) as defined above wherein X and W denote N and V and Y are CH.

$R_1$ in formula (1) is preferably hydrogen or methoxy.

$R_2$ in formula (1) is preferably hydrogen or hydroxy.

$R_3$ formula (1) is preferably hydrogen or methoxy.

The compounds of formula (1) can be prepared according to known methods, for instance by the process described in Helv. Chim. Acta 55, 1566 (1972).

Accordingly, the invention further relates to a process for the preparation of a compound of formula (1) as defined above, which comprises (I). to prepare the 2-aryl-4H-1,3-benzoxazin-4-one (4) by acid-catalysed ring closure reaction of the salicylamide derivative (2) with the carboxylic acid (3),

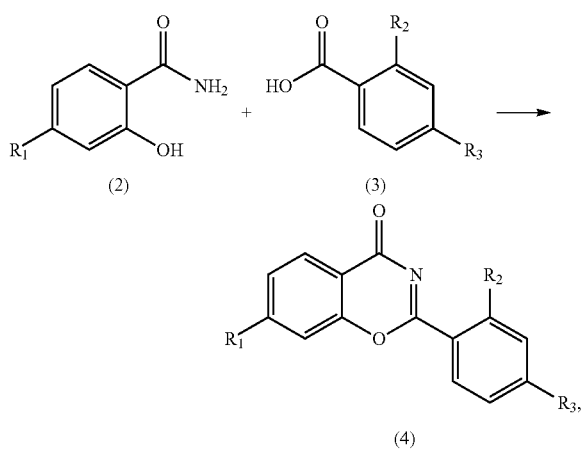

and (II). to react the thus obtained 2-aryl-4H-1,3-benzoxazin-4-one (4) with the amidine (5) to provide the triazine derivative of formula (1),

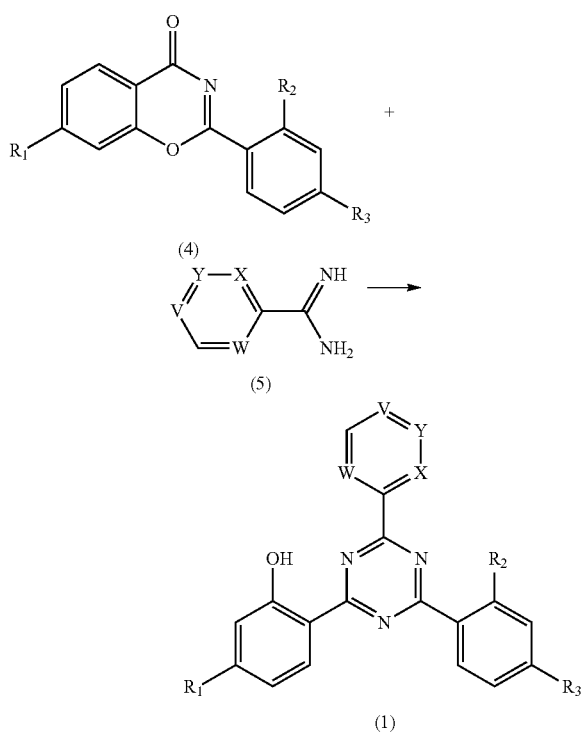

wherein $R_1$, $R_2$, $R_3$, X, Y, V and W are as defined above.

The compound of formula (1) is preferably applied in an amount of 0.01-15.0% by weight, more preferably 0.1-10.0% by weight and in particular 0.5-7.0% by weight, based on the weight of the fibre material.

The novel UVAs are especially suitable for the photochemical stabilisation of undyed, dyed or printed textile fibre materials, which is also provided by the present invention.

A corresponding process comprises treating the textile fibre materials with a liquor containing at least one compound of the above formula (1).

Textile fibre materials suitable for the treatment are primarily fibre materials containing polyester or cellulose acetate. The term polyester fibres should be understood as referring, for example, to cellulose ester fibres, such as secondary cellulose acetate fibres and triacetate fibres, and especially linear polyester fibres which may have been acid-modified, such fibres being obtained, for example, by condensation of terephthalic acid with ethylene glycol or of isophthalic acid or terephthalic acid with 1,4-bis(hydroxymethyl)cyclohexane, and also fibres of copolymers of terephthalic acid and isophthalic acid with ethylene glycol. Customary polyester fibres in the textile fibre industry consist, in particular, of terephthalic acid and ethylene glycol.

The textile fibre material to be treated may also be a blend fabric of polyester fibres and other fibres, examples being blends of polyacrylonitrile/polyester, polyamide/polyester, polyester/cotton, polyester/viscose, or polyester/wool fibres, which are printed or dyed in a customary batch or continuous procedure.

The process according to the invention is particularly suitable for the stabilisation of polyester fibres or blend fabrics of polyester fibres and other fibres, like PAN/PES, PA/PES, PES/CO and PES/WO.

The fibres can be applied in the process according to the invention in any conventional form, for example in the form of microfibers.

Accordingly, the invention further relates to a process for the stabilisation of textile fibre material, wherein the textile fibre material comprises polyester fibres.

The novel UVAs are sparingly soluble in water and are therefore applied in dispersed form. For this purpose, they are ground to particle sizes of ca. 0.1-3.0 µm in accordance with the application conditions using, for example, an appropriate dispersant and with the aid of, for example, quartz beads and a high-speed stirrer.

The application of the UVAs according to the invention can be carried out prior to, during or after the dyeing process of the textile material.

Preferably the UVA is applied simultaneously with the dyes, i.e. it is added to the dyeing liquor in the exhaust or padding process.

Accordingly, the invention relates to a process for the photochemical stabilisation of dyed textile fibre material, wherein the compound of formula (1) is applied as a part of the dyeing liquor.

The disperse dyes to be used which are only very sparingly soluble in water and are mostly present in the dyeing liquor in the form of a fine dispersion, can belong to a wide range of dye classes, for example the acridone, azo, anthraquinone, coumarin, methane, perinone, naphthoquinoneimine, quinophthalone, styryl or nitro dyes. It is also possible to use mixtures of disperse dyes in the practice of this invention.

The amount of dye to be added to the liquor will depend on the desired depth of shade; suitable amounts range in general from 0.01 to 10.0% by weight, preferably, 0.02 to 5.0% by weight, based on the textile material used.

The application of the UVA according to the invention, optionally in combination with dyeing, may take place from an aqueous liquor by a continuous or batch procedure.

In the case of continuous dyeineg procedures the dyeing liquors, which in addition to the dyes may include further auxiliaries, are applied to the piece material by means, for example, of pad-mangling, spraying or knit padding, and are developed using thermofix or HT steam processes.

In the case of the batch procedure (exhaust procedure) the liquor ratio can be chosen within a wide range, for example from 1:1 to 1:100, preferably from 1:6 to 1:50. The temperature at which dyeing is carried out is at least 50° C. and generally not more than 140° C. It is preferably within the range from 80° C. to 135° C.

The application of the UVA according to the invention is advantageously carried out by the exhaust method using an aqueous liquor. The liquor ratio is preferably from 1:3 to 1:50, especially from 1:5 to 1:30. The liquor temperature during application is preferably from 70° C. to 140° C., especially from 80° C. to 135° C.

Linear polyester fibres are preferably treated by the high temperature process in closed and pressure-resistant apparatus at temperatures>100° C., preferably between 110° C. and 135° C., and at atmospheric or superatmospheric pressures. Examples of suitable closed vessels are are circulation apparatus, such as cheese or beam dyeing apparatus, winch becks, jet or drim dyeing machines, muff dyeing apparatus, paddles or jiggers.

In addition to the compound of formula (1) and the dyes, the liquors according to the invention can comprise further customary additives, for example dyeing assistants, stabilisers, complexing agents, carriers, thickeners, dust-binding agents, anionic or non-ionic dispersants, wetting agents, separating agents, frost protection agents, antifoams, preservatives and bactericides.

The dye baths may additionally contain mineral acids, examples being sulfuric acid or phosphoric acid, or, more expediently, organic acids, for example aliphatic carboxylic acids such as formic acid, acetic acid, oxalic acid, or citric acid, and/or salts, such as ammonium acetate, ammonium sulfate or sodium acetate. The purpose of the acids in particular is to establish the pH of the liquors used in accordance with the invention, which is preferably between 4 and 6, in particular between 4.5 and 5.5.

The dyeing liquor comprising the UVA according to the invention, the dye and, where appropriate, further adjuvants is advantageously adjusted to a pH of from 4.5 to 5.5. The exhaust temperature is increased at a rate of 2° C./min from 30° C. to 135° C. and is held at that value for from 15 to 90 min.

The dyeing liquor is then cooled to from 60 to 80° C. The fibre material is washed with water and, if necessary, subjected to a clearing treatment in an alkaline medium. Afterwards the dyed fibres are rinsed again and dried.

The textile fibre material to be treated with the UVA according to the invention may be in a variety of made-up forms, for example as loose material, piece goods such as knitted or woven fabrics or as a yarn on, for example, cheeses, warp beams etc. The latter can have package densities of 200 to 600 g/l, in particular 400 to 450 g/l.

The dyeings or printings obtained by application of the compounds of formula (1) are characterised by outstanding light fastness, in particular hot light fastness properties, and are therefore especially suitable for fibres used in the automotive or swimwear sectors or in so-called "outdoor" articles.

The following Examples illustrate the invention.

I. SYNTHESIS EXAMPLES

Example 1.1

Synthesis of the Compound

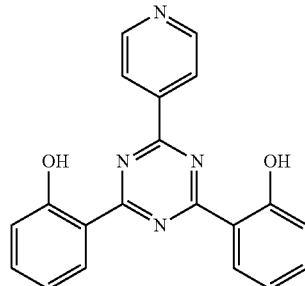

(103)

A mixture of salicylic acid (20.9 g), salicylamide (21.0 g), N,N'-dimethylformamide (0.5 ml) and xylene (70 ml) is heated to 110° C., and then thionyl chloride (36.0 g) is added dropwise. The reaction mixture is stirred for 5 hours at 126° C. After completion of reaction, the reaction mixture is gradually cooled down at 10° C. and then stirred for 1 hour. The precipitate is filtered and washed with methanol and dried under vacuum to yield 2-(2-hydroxyphenyl)-4H-1,3-benzoxazin-4-one (19.1 g).

30% sodium methylate in methanol (13.0 g) is added to the mixture of methanol (140 ml) and 4-pyridinecarboxamidine hydrochloride (7.5 g) which is prepared according to the patent of U.S. Pat. No. 6,004,965 at room temperature. Then, 2-(2-hydroxyphenyl)-4H-1,3-benzoxazin-4-one (12.1 g) is added at 35° C. The reaction mixture is stirred for 4 hours at 50° C. After cooling of the reaction mixture to room temperature, the precipitate is collected by suction filtration, washed with methanol and water and dried at 60° C. under vacuum to yield 2,4-bis(2-hydroxyphenyl)-6-(4-pyridinyl)-1,3,5-triazine (8.9 g). Melting point: 258-260° C. $\lambda_{max}$=280 nm/352 nm.

Example 1.2

Synthesis of the Compound

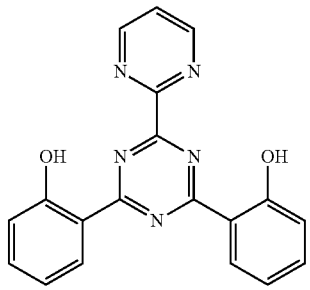

(104)

A mixture of salicylic acid (132 g), salicylamide (126 g), N,N'-dimethylformamide (3 ml) and xylene (240 ml) is heated to 110° C., and then thionyl chloride (216 g) is added dropwise. The reaction mixture is stirred for 5 hours at 126° C. After completion of reaction, the reaction mixture is gradually cooled down at 10° C. and then stirred for 1 hour.

The precipitate is filtered and washed with methanol and dried under vacuum to yield 2-(2-hydroxyphenyl)-4H-1,3-benzoxazin-4-one (143 g).

30% sodium methylate in methanol (9.0 g) is added to the mixture of methanol (140 ml) and 2-pyrimidinecarboxamidine hydrochloride (7.9 g) which is prepared according to the patent of WO 2011/024056 A2 at room temperature. Then, 2-(2-hydroxyphenyl)-4H-1,3-benzoxazin-4-one (12.6 g) is added at 35° C. The reaction mixture is stirred for 4 hours at 50° C. After cooling of the reaction mixture to room temperature, the precipitate is collected by suction filtration, washed with methanol and water and dried at 60° C. under vacuum to yield 2,4-bis(2-hydroxyphenyl)-6-(2-pyrimidinyl)-1,3,5-triazine (11.8 g). Melting point: 321-325° C. (decomposed). $\lambda_{max}$=280 nm/354 nm.

Examples 1.3-1.16

Analogously to the procedure described in Example 1.1, the compounds listed in Table 1 are prepared.

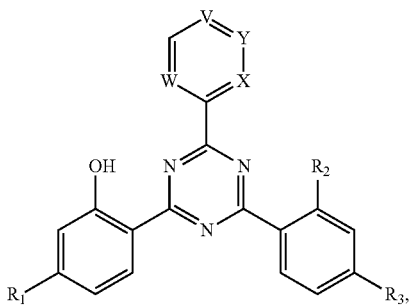

(1)

TABLE 1

| Compound | $R_1$ | $R_2$ | $R_3$ | V | W | X | Y |
|---|---|---|---|---|---|---|---|
| (105) | H | H | H | N | CH | CH | CH |
| (106) | H | CH$_3$ | H | N | CH | CH | CH |
| (107) | H | OCH$_3$ | H | N | CH | CH | CH |
| (108) | H | Cl | H | N | CH | CH | CH |
| (109) | H | Br | H | N | CH | CH | CH |
| (110) | H | H | H | CH | CH | CH | N |
| (111) | H | OH | H | CH | CH | CH | N |
| (112) | H | CH$_3$ | H | CH | CH | CH | N |
| (113) | H | OCH$_3$ | H | CH | CH | CH | N |
| (114) | H | Cl | H | CH | CH | CH | N |
| (115) | H | Br | H | CH | CH | CH | N |
| (116) | H | H | H | CH | CH | N | CH |
| (117) | H | CH$_3$ | H | CH | CH | N | CH |
| (118) | H | OCH$_3$ | H | CH | CH | N | CH |
| (119) | H | Cl | H | CH | CH | N | CH |
| (120) | H | Br | H | CH | CH | N | CH |
| (121) | H | H | H | CH | N | N | CH |
| (122) | H | CH$_3$ | H | CH | N | N | CH |
| (123) | H | OCH$_3$ | H | CH | N | N | CH |
| (124) | H | Cl | H | CH | N | N | CH |
| (125) | H | Br | H | CH | N | N | CH |
| (126) | H | H | CH$_3$ | N | CH | CH | CH |
| (127) | H | H | OCH$_3$ | N | CH | CH | CH |
| (128) | H | H | CN | N | CH | CH | CH |
| (129) | H | H | CF$_3$ | N | CH | CH | CH |
| (130) | H | H | Cl | N | CH | CH | CH |
| (131) | H | H | Br | N | CH | CH | CH |
| (132) | H | H | CH$_3$ | CH | CH | CH | N |
| (133) | H | H | OCH$_3$ | CH | CH | CH | N |
| (134) | H | H | CN | CH | CH | CH | N |
| (135) | H | H | CF$_3$ | CH | CH | CH | N |
| (136) | H | H | Cl | CH | CH | CH | N |
| (137) | H | H | Br | CH | CH | CH | N |
| (138) | H | H | CH$_3$ | CH | CH | N | CH |
| (139) | H | H | OCH$_3$ | CH | CH | N | CH |
| (140) | H | H | CN | CH | CH | N | CH |
| (141) | H | H | CF$_3$ | CH | CH | N | CH |
| (142) | H | H | Cl | CH | CH | N | CH |
| (143) | H | H | Br | CH | CH | N | CH |
| (144) | H | H | CH$_3$ | CH | N | N | CH |
| (145) | H | H | OCH$_3$ | CH | N | N | CH |
| (146) | H | H | CN | CH | N | N | CH |
| (147) | H | H | CF$_3$ | CH | N | N | CH |
| (148) | H | H | Cl | CH | N | N | CH |
| (149) | H | H | Br | CH | N | N | CH |
| (150) | H | OH | CH$_3$ | N | CH | CH | CH |
| (151) | H | OH | OCH$_3$ | N | CH | CH | CH |
| (152) | H | OH | CF$_3$ | N | CH | CH | CH |
| (153) | H | OH | Cl | N | CH | CH | CH |
| (154) | H | OH | Br | N | CH | CH | CH |
| (155) | H | OH | CH$_3$ | CH | CH | CH | N |
| (156) | H | OH | OCH$_3$ | CH | CH | CH | N |
| (157) | H | OH | CF$_3$ | CH | CH | CH | N |
| (158) | H | OH | Cl | CH | CH | CH | N |
| (159) | H | OH | Br | CH | CH | CH | N |
| (160) | H | OH | CH$_3$ | CH | CH | N | CH |
| (161) | H | OH | OCH$_3$ | CH | CH | N | CH |
| (162) | H | OH | CF$_3$ | CH | CH | N | CH |
| (163) | H | OH | Cl | CH | CH | N | CH |
| (164) | H | OH | Br | CH | CH | N | CH |
| (165) | H | OH | CH$_3$ | CH | N | N | CH |
| (166) | H | OH | OCH$_3$ | CH | N | N | CH |
| (167) | H | OH | CF$_3$ | CH | N | N | CH |
| (168) | H | OH | Cl | CH | N | N | CH |
| (169) | H | OH | Br | CH | N | N | CH |
| (170) | CH$_3$ | H | H | N | CH | CH | CH |
| (171) | CH$_3$ | H | CH$_3$ | N | CH | CH | CH |
| (172) | CH$_3$ | H | OCH$_3$ | N | CH | CH | CH |
| (173) | CH$_3$ | H | CN | N | CH | CH | CH |
| (174) | CH$_3$ | H | CF$_3$ | N | CH | CH | CH |
| (175) | CH$_3$ | H | Cl | N | CH | CH | CH |
| (176) | CH$_3$ | H | Br | N | CH | CH | CH |
| (177) | CH$_3$ | H | H | CH | CH | CH | N |
| (178) | CH$_3$ | H | CH$_3$ | CH | CH | CH | N |
| (179) | CH$_3$ | H | OCH$_3$ | CH | CH | CH | N |
| (180) | CH$_3$ | H | CN | CH | CH | CH | N |
| (181) | CH$_3$ | H | CF$_3$ | CH | CH | CH | N |
| (182) | CH$_3$ | H | Cl | CH | CH | CH | N |
| (183) | CH$_3$ | H | Br | CH | CH | CH | N |
| (184) | CH$_3$ | H | H | CH | CH | N | CH |
| (185) | CH$_3$ | H | CH$_3$ | CH | CH | N | CH |
| (186) | CH$_3$ | H | OCH$_3$ | CH | CH | N | CH |
| (187) | CH$_3$ | H | CN | CH | CH | N | CH |
| (188) | CH$_3$ | H | CF$_3$ | CH | CH | N | CH |
| (189) | CH$_3$ | H | Cl | CH | CH | N | CH |
| (190) | CH$_3$ | H | Br | CH | CH | N | CH |
| (191) | CH$_3$ | H | H | CH | N | N | CH |
| (192) | CH$_3$ | H | CH$_3$ | CH | N | N | CH |
| (193) | CH$_3$ | H | OCH$_3$ | CH | N | N | CH |
| (194) | CH$_3$ | H | CN | CH | N | N | CH |
| (195) | CH$_3$ | H | CF$_3$ | CH | N | N | CH |
| (196) | CH$_3$ | H | Cl | CH | N | N | CH |
| (197) | CH$_3$ | H | Br | CH | N | N | CH |
| (198) | OCH$_3$ | H | H | N | CH | CH | CH |
| (199) | OCH$_3$ | H | CH$_3$ | N | CH | CH | CH |
| (200) | OCH$_3$ | H | OCH$_3$ | N | CH | CH | CH |
| (201) | OCH$_3$ | H | CN | N | CH | CH | CH |
| (202) | OCH$_3$ | H | CF$_3$ | N | CH | CH | CH |
| (203) | OCH$_3$ | H | Cl | N | CH | CH | CH |
| (204) | OCH$_3$ | H | Br | CH | CH | CH | N |
| (205) | OCH$_3$ | H | H | CH | CH | CH | N |
| (206) | OCH$_3$ | H | CH$_3$ | CH | CH | CH | N |
| (207) | OCH$_3$ | H | OCH$_3$ | CH | CH | CH | N |
| (208) | OCH$_3$ | H | CN | CH | CH | CH | N |
| (209) | OCH$_3$ | H | CF$_3$ | CH | CH | CH | N |
| (210) | OCH$_3$ | H | Cl | CH | CH | CH | N |
| (211) | OCH$_3$ | H | Br | CH | CH | CH | N |
| (212) | OCH$_3$ | H | H | CH | CH | N | CH |
| (213) | OCH$_3$ | H | CH$_3$ | CH | CH | N | CH |
| (214) | OCH$_3$ | H | OCH$_3$ | CH | CH | N | CH |

TABLE 1-continued

| Compound | $R_1$ | $R_2$ | $R_3$ | V | W | X | Y |
|---|---|---|---|---|---|---|---|
| (215) | OCH$_3$ | H | CN | CH | CH | N | CH |
| (216) | OCH$_3$ | H | CF$_3$ | CH | CH | N | CH |
| (217) | OCH$_3$ | H | Cl | CH | CH | N | CH |
| (218) | OCH$_3$ | H | Br | CH | CH | N | CH |
| (219) | OCH$_3$ | H | H | CH | N | N | CH |
| (220) | OCH$_3$ | H | CH$_3$ | CH | N | N | CH |
| (221) | OCH$_3$ | H | OCH$_3$ | CH | N | N | CH |
| (222) | OCH$_3$ | H | CN | CH | N | N | CH |
| (223) | OCH$_3$ | H | CF$_3$ | CH | N | N | CH |
| (224) | OCH$_3$ | H | Cl | CH | N | N | CH |
| (225) | OCH$_3$ | H | Br | CH | N | N | CH |
| (226) | CH$_3$ | OH | CH$_3$ | N | CH | CH | CH |
| (227) | CH$_3$ | OH | OCH$_3$ | N | CH | CH | CH |
| (228) | CH$_3$ | OH | CF$_3$ | N | CH | CH | CH |
| (229) | CH$_3$ | OH | Cl | N | CH | CH | CH |
| (230) | CH$_3$ | OH | Br | N | CH | CH | CH |
| (231) | CH$_3$ | OH | CH$_3$ | CH | CH | CH | N |
| (232) | CH$_3$ | OH | OCH$_3$ | CH | CH | CH | N |
| (233) | CH$_3$ | OH | CF$_3$ | CH | CH | CH | N |
| (234) | CH$_3$ | OH | Cl | CH | CH | CH | N |
| (235) | CH$_3$ | OH | Br | CH | CH | CH | N |
| (236) | CH$_3$ | OH | CH$_3$ | CH | CH | N | CH |
| (237) | CH$_3$ | OH | OCH$_3$ | CH | CH | N | CH |
| (238) | CH$_3$ | OH | CF$_3$ | CH | CH | N | CH |
| (239) | CH$_3$ | OH | Cl | CH | CH | N | CH |
| (240) | CH$_3$ | OH | Br | CH | CH | N | CH |
| (241) | CH$_3$ | OH | CH$_3$ | CH | N | N | CH |
| (242) | CH$_3$ | OH | OCH$_3$ | CH | N | N | CH |
| (243) | CH$_3$ | OH | CF$_3$ | CH | N | N | CH |
| (244) | CH$_3$ | OH | Cl | CH | N | N | CH |
| (245) | CH$_3$ | OH | Br | CH | N | N | CH |
| (246) | OCH$_3$ | OH | OCH$_3$ | N | CH | CH | CH |
| (247) | OCH$_3$ | OH | CF$_3$ | N | CH | CH | CH |
| (248) | OCH$_3$ | OH | Cl | N | CH | CH | CH |
| (249) | OCH$_3$ | OH | Br | N | CH | CH | CH |
| (250) | OCH$_3$ | OH | OCH$_3$ | CH | CH | CH | N |
| (251) | OCH$_3$ | OH | CF$_3$ | CH | CH | CH | N |
| (252) | OCH$_3$ | OH | Cl | CH | CH | CH | N |
| (253) | OCH$_3$ | OH | Br | CH | CH | CH | N |
| (254) | OCH$_3$ | OH | CF$_3$ | CH | CH | N | CH |
| (255) | OCH$_3$ | OH | Cl | CH | CH | N | CH |
| (256) | OCH$_3$ | OH | Br | CH | CH | N | CH |
| (257) | OCH$_3$ | OH | OCH$_3$ | CH | N | N | CH |
| (258) | OCH$_3$ | OH | CF$_3$ | CH | N | N | CH |
| (259) | OCH$_3$ | OH | Cl | CH | N | N | CH |
| (260) | OCH$_3$ | OH | Br | CH | N | N | CH |

II. APPLICATION EXAMPLES

II.1. Dyeing of Polyester

Specimens of 10 g of a PES knit-fabric (5-4212) are dyed by a laboratory high temperature dyeing machine Labomat BFA-16 (Mathis) with a dyeing liquor containing 1.0 g/l ammonium sulphate,
0.5 g/l wetting agent,
1.0 g/l dispersing agent, as well as the 0.218% by weight, based on the weight of the fabric, of the dyestuff Teratop® Yellow HL-G-01 150% (supplied by Huntsman), 0.112% by weight, based on the weight of the fabric, of the dyestuff Teratop® Red HL (supplied by Huntsman), and 0.142% by weight, based on the weight of the fabric, of the dyestuff Teratop® Blue HL-B 150% (supplied by Huntsman) and the compound of formula (103), (111) or (127), respectively, in the amounts given in Table 2 according to the exhaust method (liquor ratio 1:20, 60 min/135° C.). After cooling to about 80° C. the specimens are subjected to a reductive aftertreatment (20 min/75° C.) with a clearing liquor containing 2.0 g/l sodium hydrosulfite,
5.0 g/l 30% NaOH,
1.0 g/l soaping agent (Eriopon® OS, supplied by Huntsman) and subsequently rinsed with water and dried.

The dyeings so obtained are tested for hot lightfastness according to DIN 75202 (FAKRA).

The results are summarised in Table 2.

The percentages in Table 2 are % by weight and relate to the weight of the fabric.

TABLE 2

| Hot ligthfastness ratings* of grey dyeings obtained with different amounts of UVA | | | |
|---|---|---|---|
| Amount UVA | (103) | (111) | (127) |
| 0% | 2.5 | 2.5 | 2.5 |
| 2% | 3.1 | 3.1 | 3.3 |
| 4% | 3.4 | 3.6 | 3.7 |
| 6% | 3.6 | 3.6 | 3.8 |

*1 to 5 decimal rating according to grey scale ISO 105-A02

II.2. Dyeing of Polyester

Specimens of 10 g of a PES knit-fabric (5-4212) are dyed by a laboratory high temperature dyeing machine Labomat BFA-16 (Mathis) with a dyeing liquor containing 1.0 g/l ammonium sulphate,
0.5 g/l wetting agent,
1.0 g/l dispersing agent, as well as the 0.20% by weight, based on the weight of the fabric, of the dyestuff Teratop® Yellow HL-G-01 150% (supplied by Huntsman), 0.11% by weight, based on the weight of the fabric, of the dyestuff Teratop® Red HL (supplied by Huntsman), and 0.26% by weight, based on the weight of the fabric, of the dyestuff Teratop® Blue HL-GR (supplied by Huntsman) and the compound of formula (110), (116), (121), (133) or (145), respectively, in the amounts given in Table 3 according to the exhaust method (liquor ratio 1:20, 60 min/135° C.).

After cooling to about 80° C. the specimens are subjected to a reductive aftertreatment (20 min/75° C.) with a clearing liquor containing 2.0 g/l sodium hydrosulfite,
5.0 g/l 30% NaOH,
1.0 g/l soaping agent (Eriopon® OS, supplied by Huntsman)

and subsequently rinsed with water and dried.

The dyeings so obtained are tested for hot lightfastness according to DIN 75202 (FAKRA).

The results are summarised in Table 3.

The percentages in Table 3 are % by weight and relate to the weight of the fabric.

TABLE 3

| Hot ligthfastness ratings* of grey dyeings obained with different amounts of UVA | | | | | |
|---|---|---|---|---|---|
| Amount UVA | (110) | (116) | (121) | (133) | (145) |
| 0% | 2.6 | 2.6 | 2.7 | 2.7 | 2.7 |
| 2% | 3.5 | 3.8 | 3.6 | 3.8 | 3.8 |
| 4% | 3.8 | 4.0 | 3.9 | 3.9 | 4.1 |
| 6% | 3.9 | 4.1 | 3.9 | 4.2 | 4.1 |

*1 to 5 decimal rating according to grey scale ISO 105-A02

What is claimed is:

1. A compound of formula

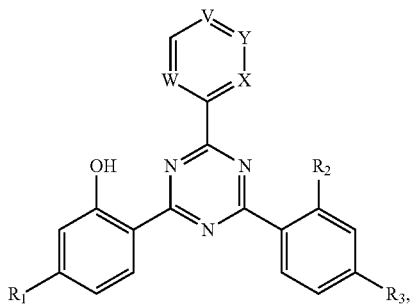

wherein X and W denote N and V and Y are CH; and $R_1$, $R_2$ and $R_3$ are each independently of the other hydrogen, $C_1$-$C_8$ alkyl, $C_1$-$C_8$ alkoxy, nitro, cyano, trifluoromethyl, halogen or hydroxy;

with the proviso that the compounds of formulae (101)

(102)

are excluded.

2. The compound of formula (1) according to claim 1, wherein $R_1$ is hydrogen or methoxy.

3. The compound of formula (1) according to claim 1, wherein $R_2$ is hydrogen or hydroxy.

4. The compound of formula (1) according to claim 1, wherein $R_3$ is hydrogen or methoxy.

5. The process for the preparation of a compound of formula (1) according to claim 1, which comprises (I) to prepare the 2-aryl-4H-1,3-benzoxazin-4-one (4) by acid-catalysed ring closure reaction of the salicylamide derivative (2) with the carboxylic acid (3),

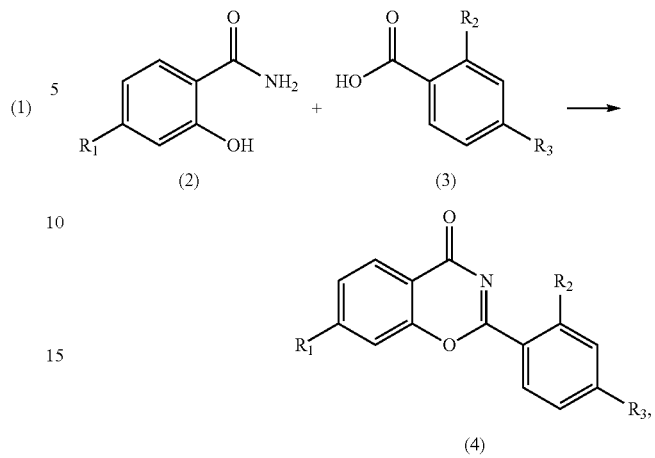

and (II) to react the thus obtained 2-aryl-4H-1,3-benzoxazin-4-one (4) with the amidine (5) to provide the triazine derivative of formula (1),

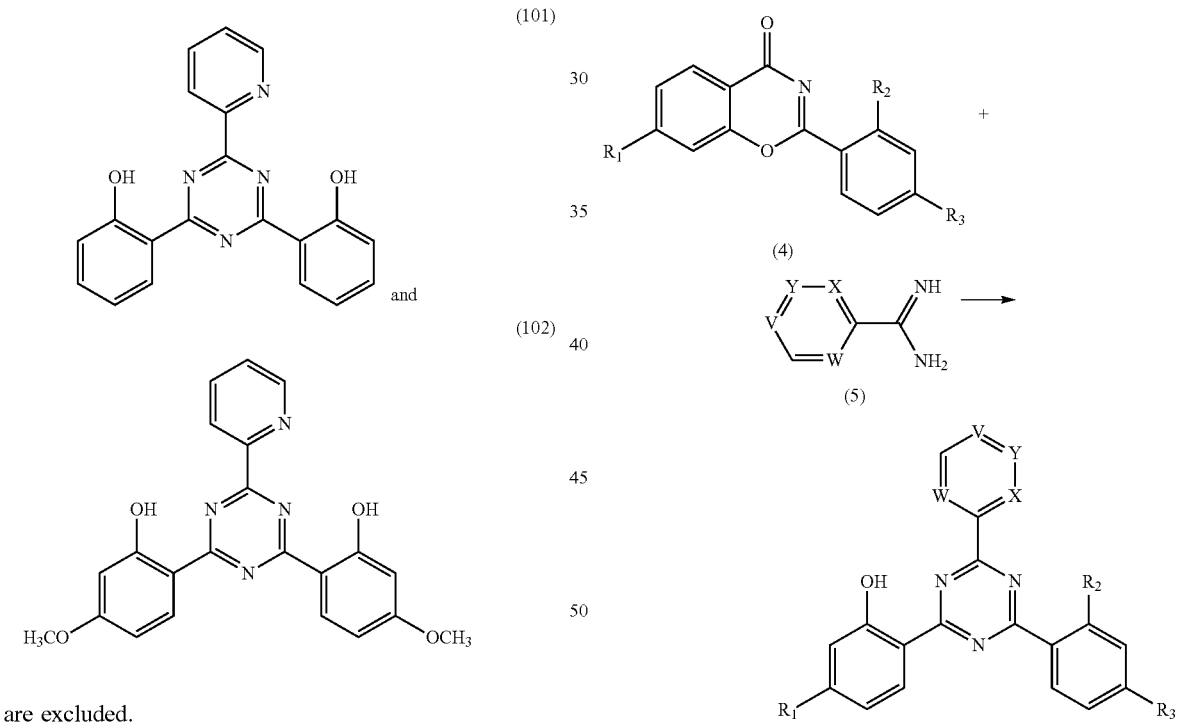

wherein $R_1$, $R_2$, $R_3$, X, Y, V and W are as defined in claim 1.

6. The process for the photochemical stabilisation of undyed, dyed or printed textile fibre material, which comprises treating the textile fibre material with a liquor containing at least one compound of formula (1) according to claim 1.

7. The process according to claim 6, wherein the textile fibre material comprises polyester fibres.

8. The process for the photochemical stabilisation of dyed textile fibre material according to claim 6, wherein the compound of formula (1) is applied as a part of the dyeing liquor.

* * * * *